(12) United States Patent
Cho et al.

(10) Patent No.: US 8,703,939 B2
(45) Date of Patent: Apr. 22, 2014

(54) METHOD FOR PREPARING (R)-3-(3-FLUORO-4-(1-METHYL-5,6-DIHYDRO-1,2,4-TRIAZIN-4(1H)-YL) PHENYL)-5-(SUBSTITUTED METHYL)OXAZOLIDIN-2-ONE DERIVATIVES

(75) Inventors: Young Lag Cho, Daejeon (KR); Sung Yoon Baek, Daejeon (KR); Sang Eun Chae, Daejeon (KR); Hong Bum Lee, Daejeon (KR); Tae Kyo Park, Daejeon (KR); Sung Ho Woo, Daejeon (KR); Yong Zu Kim, Daejeon (KR)

(73) Assignee: Legochem Biosciences, Inc., Daejeon (KR)

( * ) Notice: Subject to any disclaimer, the term of this patent is extended or adjusted under 35 U.S.C. 154(b) by 0 days.

(21) Appl. No.: 13/583,492

(22) PCT Filed: Mar. 8, 2011

(86) PCT No.: PCT/KR2011/001579
§ 371 (c)(1),
(2), (4) Date: Sep. 7, 2012

(87) PCT Pub. No.: WO2011/111971
PCT Pub. Date: Sep. 15, 2011

(65) Prior Publication Data
US 2013/0005967 A1 Jan. 3, 2013

(30) Foreign Application Priority Data
Mar. 8, 2010 (KR) .......................... 10-2010-0020525

(51) Int. Cl.
*C07D 253/065* (2006.01)
*C07D 413/10* (2006.01)
*C07D 413/14* (2006.01)

(52) U.S. Cl.
USPC ........................................... 544/182

(58) Field of Classification Search
USPC .......................................................... 544/182
See application file for complete search history.

(56) References Cited

U.S. PATENT DOCUMENTS 8,242,113 B2 * 8/2012 Cho et al. .................... 514/229.2

FOREIGN PATENT DOCUMENTS

| EP | 2 072 513 A1 | 6/2009 |
|---|---|---|
| EP | 2 072 514 A1 | 6/2009 |
| EP | 2 141 161 A1 | 1/2010 |
| EP | 2 141 162 A1 | 1/2010 |
| WO | 03/035648 A1 | 5/2003 |
| WO | 2004/048350 A2 | 6/2004 |
| WO | 2004/056819 A1 | 7/2004 |
| WO | 2010/036000 A2 | 4/2010 |

OTHER PUBLICATIONS

Schulz et al., Chemische Berichte, 122(10), 1983-7, 1989 (CAPLUS abstract provided).*
Minlibaeva et al. Org. Khim., 99-102, 1976 (CAPLUS abstract provided).*
International Search Report of PCT/KR2011/001579 dated Nov. 22, 2011.

* cited by examiner

*Primary Examiner* — Venkataraman Balasubramanian
(74) *Attorney, Agent, or Firm* — Sughrue Mion, PLLC

(57) ABSTRACT

Provided are a method for preparing (R)-3-(3-fluoro-4-(1-methyl-5, 6-dihydro-1,2,4-triazin-4(1H)-yl)phenyl)-5-(substituted methyl) oxazolidin-2-one derivatives, which are oxazolidinone antibiotic compounds having a cyclic amidrazone group, represented by Chemical Formula 1, and intermediates thereof, and uses 3,4-difluoro-4-nitrobenzen as a starting material. According to the preparation method of the present invention, (R)-3-(3-fluoro-4-(1-methyl-5, 6-dihydro-1,2,4-triazin-4(1H)-yl)phenyl)-5-(substituted methyl) oxazolidin-2-one derivatives, which are useful as oxazolidinone antibiotics, can be prepared in high purity and high yield in a simpler manner than conventional methods.

5 Claims, No Drawings

METHOD FOR PREPARING (R)-3-(3-FLUORO-4-(1-METHYL-5,6-DIHYDRO-1,2,4-TRIAZIN-4(1H)-YL)PHENYL)-5-(SUBSTITUTED METHYL)OXAZOLIDIN-2-ONE DERIVATIVES

TECHNICAL FIELD

The following disclosure relates to a method for preparing (R)-3-(3-fluoro-4-(1-methyl-5,6-dihydro-1,2,4-triazin-4(1H)-yl)phenyl)-5-(substituted methyl)oxazolidin-2-one derivatives, which are oxazolidinone antibiotic compounds having a cyclic amidrazone group, represented by Chemical Formula 1, and intermediates thereof.

[Chemical Formula 1]

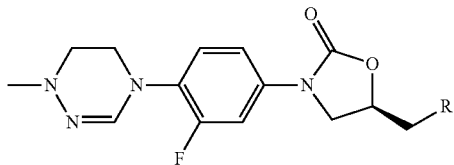

In Chemical Formula, R is —OH or —NHC(=O)R$_1$; and R$_1$ is (C1-C6)alkyl or (C1-C6)alkoxy.

BACKGROUND ART

Compound 1a ((R)-3-(3-fluoro-4-(1-methyl-5,6-dihydro-1,2,4-triazin-4(1H)-yl)phenyl)-5-(hydroxymethyl)oxazolidin-2-one) having the following structure is an oxazolidinone antibiotic and may be used to treat infections by Gram-positive bacteria, and particularly, methicillin-resistant staphylococci (MRSA), vancomycin resistant enterococci (VRE), or the like.

compound 1a

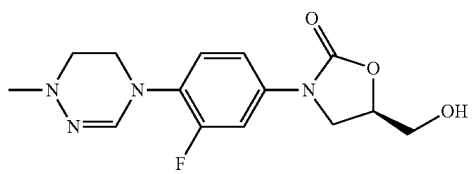

An antibiotic effect of the compound and a method for preparing the same have been disclosed in Korea Patent Application No. 10-2008-0093712 filed by the present inventor. However, since the overall reaction step of the preparing method is long, and column chromatography should be used in most of the purifying processes for each step, such that the method is not appropriate for mass production.

DISCLOSURE

Technical Problem

An object of the present invention is to provide a method for preparing (R)-3-(3-fluoro-4-(1-methyl-5,6-dihydro-1,2,4-triazin-4(1H)-yl)phenyl)-5-(substituted methyl)oxazolidin-2-one derivatives by reducing the overall reaction step and using a crystallization method or an extraction method appropriate for an industrial scale synthesis to more simply and economically prepare thereof in high purity as compared to the related art.

In addition, an embodiment of the present invention is directed to providing preparation intermediates used to prepare (R)-3-(3-fluoro-4-(1-methyl-5,6-dihydro-1,2,4-triazin-4(1H)-yl)phenyl)-5-(substituted methyl)oxazolidin-2-one derivatives, and a method for preparing the same.

Technical Solution

In one general aspect of the present invention, there is provided a method for preparing of (R)-3-(3-fluoro-4-(1-methyl-5,6-dihydro-1,2,4-triazin-4(1H)-yl)phenyl)-5-(substituted methyl)oxazolidin-2-one derivatives of Chemical Formula 1, which are useful compounds as oxazolidinone antibiotics, and intermediates thereof.

In addition, the compound of the following Chemical Formula 1 may be prepared as various salt forms thereof, and the present invention includes these salt forms thereof. This method may be applied in an industrial scale, and particularly, the method for preparing of the compound of Chemical Formula 1 according to the present invention includes a new synthetic method for preparing a cyclic amidrazone group. Further, for a chemical method for preparing the compound appropriate for the industrial scale, the present invention includes a method for preparing intermediates having an advantage in cost-effective crystallization or salts thereof.

[Chemical Formula 1]

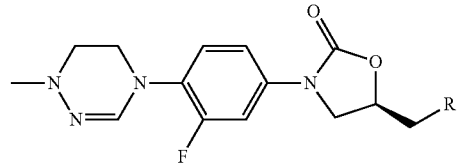

In Chemical Formula, R is —OH or —NHC(=O)R$_1$; and R$_1$ is (C1-C6)alkyl or (C1-C6)alkoxy.

A method for preparing the compound of Chemical Formula 1 is shown in the following Reaction Formula 1.

[Reaction Formula 1]

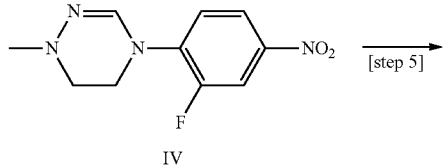

IV

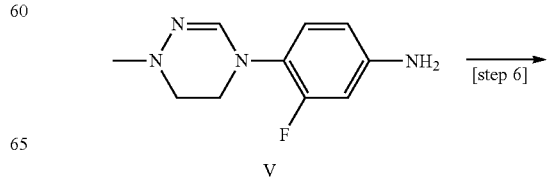

V

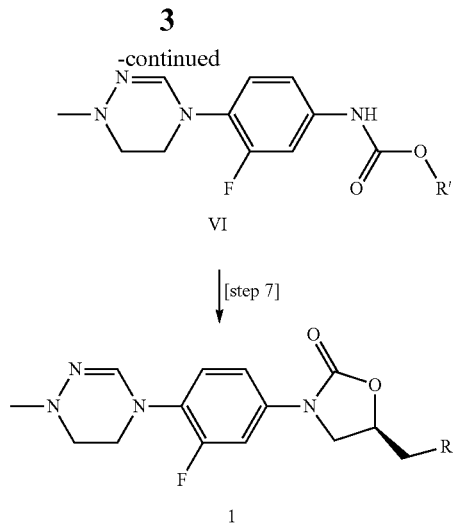

In Reaction Formula 1, R is —OH or —NHC(=O)R$_1$; R$_1$ is (C1-C6)alkyl or (C1-C6)alkoxy; and R' is (C1-C6)alkyl or (C6-C12) aryl (C1-C6) alkyl.

Each Compound of Chemical Formula IV, which is a starting material for preparing the compound of Chemical Formula 1, is prepared as shown in the following Reaction Formula 2.

1) reacting 3,4-difluoronitrobenzene and ethanolamine with each other to prepare a compound of Chemical Formula I;

2) reacting the compound of Chemical Formula I with an agent containing a leaving group X to convert an alcohol group of the compound of Chemical Formula I into the leaving group X, thereby preparing a compound of Chemical Formula II-1 (step 2-1), or reacting the compound of Chemical Formula I in the presence of base to prepare an aziridine compound of Chemical Formula II-2 (step 2-2);

3) reacting the compound of Chemical Formula II-1 or the compound of Chemical Formula II-2 with methyl hydrazine to prepare a compound of Chemical Formula III;

4) reacting the compound of Chemical Formula III with trimethyl orthoformate to prepare a cyclic amidrazone of Chemical Formula IV;

5) reducing a nitro group of the cyclic amidrazone of Chemical Formula IV to prepare an amine compound of Chemical Formula V;

6) sequentially reacting the amine compound of Chemical Formula V with carbonyl diimidazole and R'—OH [R'=(C1-C6)alkyl or (C6-C12)aryl(C1-C6)alkyl] to convert the amine group of the compound of Chemical Formula V into carbamate, thereby preparing a compound of Chemical Formula VI; and 7) cyclizing the compound of Chemical Formula VI to prepare the oxazolidinone compound of Chemical Formula 1.

[Reaction Formula 2]

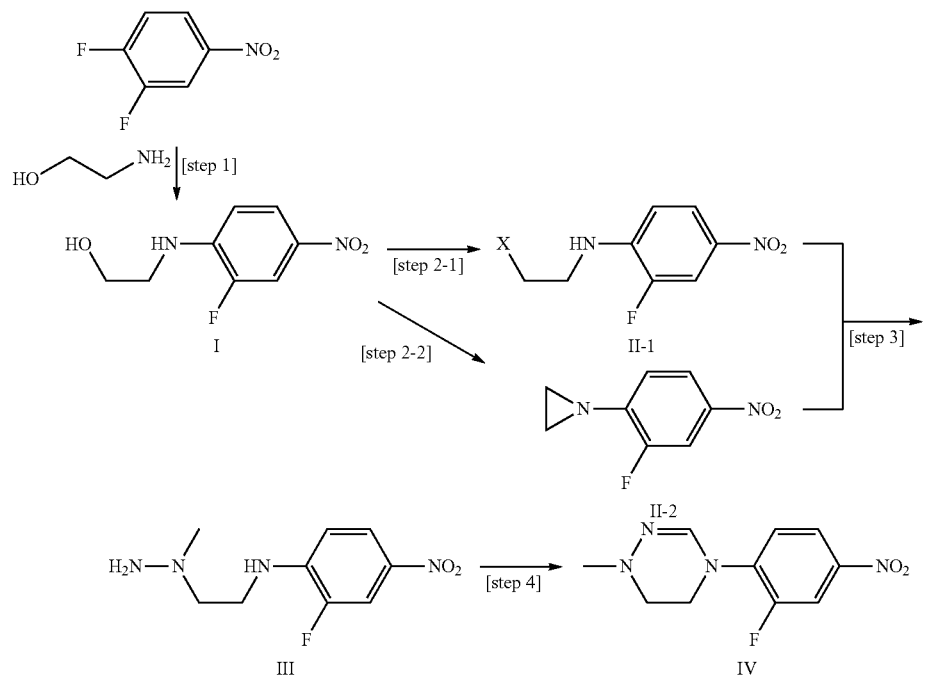

In Reaction Formula 2, X is halogen, substituted or unsubstituted (C1-C6)alkanesulfonyloxy, or substituted or unsubstituted (C6-C12)arylsulfonyloxy.

The present invention provides a method for preparing the oxazolidinone derivatives having the cyclic amidrazone group of Chemical Formula 1, and pharmaceutically acceptable salts thereof, as shown in Reaction Formulas 1 and 2, the method including:

Hereinafter, each step will be described in detail.

[Step 1] Synthesis of the Compound of Chemical Formula I

In order to prepare the compound represented by Chemical Formula I, 3,4-difluoronitrobenzen and ethanolamine that are the starting materials was refluxed and stirred in organic solvent. In this case, as examples of usable solvent include nitriles such as acetonitrile, or the like; alcohols such as ethanol, isopropanol, or the like; ethers such as tetrahydrofuran, diisopropyl ether, dioxane, 1,2-dimethoxyethane, or the like, aromatic hydrocarbons such as benzene, toluene, or the like, and amides such as dimethylamide, dimethylformamide, or the like. However, the present invention is not limited to theses inert solvents, but may use a single solvent or a mixture thereof. Preferably, acetonitrile, isopropanol, and dioxane may be used, and more preferably, acetonitrile may be used.

This reaction may be performed in the presence or absence of the base according to the amount of ethanolamine used. For example, in the case in which 1 equivalent of ethanolamine is used based on 3,4-difluoronitrobenzene, the base may be preferably used, and in the case in which excessive amount, that is, 1 equivalent or more of ethanolamine is used, the base may not be used. In the reaction in which excessive ethanolamine is used, 1.5 to 3 equivalents of ethanolamine may be preferably used. Here, as a usable base, an organic base such as triethylamine or diethylisopropylamine, or an inorganic base such as potassium carbonate, sodium carbonate may be used and preferably, may be used in a range of 1.1 to 2 equivalents.

[Step 2] Synthesis of Compounds of Chemical Formulas II-1 and II-2

The compound of Chemical Formula II-1 is obtained by reacting the compound represented by Chemical Formula I with an agent containing a leaving group X to convert an alcohol group of the compound of Chemical Formula I into the leaving group X. As the appropriate leaving group, in the case in which the leaving group X indicates a halogen atom, the X is chlorine bromine, or iodine. In the case in which the leaving group X indicates a sulfonyloxy group, examples of the leaving group preferably includes a substituted or un-substituted (C1-C6)alkanesulfonyloxy group (for example, methanesulfonyloxy, ethanesulfonyloxy, or trifluoromethanesulfonyloxy), or a substituted or un-substituted (C6-C12)arylsulfonyloxy group (for example, benzenesulfonyloxy, p-toluenesulfonyloxy, p-bromophenylsulfonyloxy, p-nitrobenzenesulfonyloxy), but is not limited thereto. Conversion of the alcohol group into the leaving group, for example, chloro, bromo, mesylate, tosylate, and benzenesulfonate, is known in the art. The reaction may be preferably performed in non-polar organic solvent such as dichloromethane, and amines such as triethylamine may be preferably used as a base.

The compound of Chemical Formula II-2 is obtained by stirring the compound represented by Chemical Formula I for 12 hours or more, and maximally, for 72 hours in the presence of triphenylphosphine and a base. The base used in this reaction may be preferably triethylamine, and as the solvent, ethers such as tetrahydrofuran (THF) or most of the non-polar solvents may be used, and preferably, a mixture of THF and tetrachloromethane may be used.

[Step 3] Synthesis of the Compound of Chemical Formula III

The compound of Chemical Formula III is obtained by reacting the compound of Chemical Formula II-1 or II-2 with methyl hydrazine. Here, various polar organic solvents in addition to alcohols such as ethanol, or the like may be used as solvent. When the compound of Chemical Formula III is obtained from the compound of Chemical Formula II-2, a purifying process is omitted in the reaction of Chemical Formula II-2 and methyl hydrazine is added to a reaction vessel, thereby making it possible to directly obtain the compound of Chemical Formula III.

5 to 10 equivalents of methyl hydrazine may be preferably used in the reaction, and a reaction temperature may be 20 to 80° C.

[Step 4] Synthesis of the Compound of Chemical Formula IV

The compound of Chemical Formula IV is obtained by forming cyclic amidrazone ring from the compound of Chemical Formula III. The reaction may be performed by reacting the compound of Chemical Formula III with orthoformate, or the like, in acetic acid or by formylating the compound of Chemical Formula III with formic acid and then cyclizing the reactant. Preferably, the compound of Chemical Formula IV is obtained by refluxing and stirring the compound of Chemical Formula III and excessive trimethyl orthoformate using acetic acid as the solvent. More preferably, 20 to 50% acetic acid mixed with 2 to 10 equivalents of trimethyl orthoformate may be used as the solvent.

[Step 5] Synthesis of the Compound of Chemical Formula V

The amine compound represented by Chemical Formula V is obtained by the reduction reaction of the nitro group of the cyclic amidrazone compound of Chemical Formula IV. Examples of the solvent used in this reaction include alcohols such as methanol, ethanol, propanol, or the like and ethers such as tetrahydrofuran, diisopropyl ether, dioxane, 1,2-dimethoxyethane, or the like. This reduction of the nitro group is well known, and may be performed using a metal such as zinc, iron, tin, tin chloride, or the like under an acidic condition, or by hydrogenation using a transition metal such as Raney-nickel, palladium-carbon, or the like as a catalyst. Preferably, the reduction reaction may be performed by stirring under hydrogen gas using palladium-carbon as the catalyst in alcohol solvent.

[Step 6] Synthesis of the Compound of Chemical Formula VI

The carbamate compound represented by Chemical Formula VI may be obtained by reacting the amine group of Chemical Formula V with carbonyl diimidazole, and then by treating the resultant with alcohol or alkoxide. Further, in the present reaction, chloroformate derivatives or phosgene may be used but are toxic to use in mass production, and carbonate derivatives may be used but has weak reactivity. Therefore, in the present invention, carbonyl diimidazole is preferably used.

Examples of alcohol R'—OH [here, R' is (C1-C6)alkyl or (C6-C12)aryl(C1-C6)alkyl] that may used in the present invention is preferably alkyl alcohols such as methyl-, ethyl-, propyl-alcohol, or the like, or benzyl alcohols. Further, in this reaction, a mixture of alcohol and alkoxide may be used. In this case, the reaction is more rapidly progressed and immediately terminated at room temperature. This reaction may be performed by adding ethyl alkoxide at room temperature using ethanol as the solvent or by heating in ethanol solvent.

[Step 7] Synthesis of the Compound of Chemical Formula 1

As a synthetic method of oxazolidinone compound of Chemical Formula 1 from the carbamate compound of Chemical Formula VI, various methods are known. Here, various methods may be selected according to an R group of Chemical Formula 1. An example of these reactions is shown in Reaction Formula 3, and Reaction Formula 3 is only one example of these reactions. Therefore, the present invention is not limited thereto.

[Reaction Formula 3]

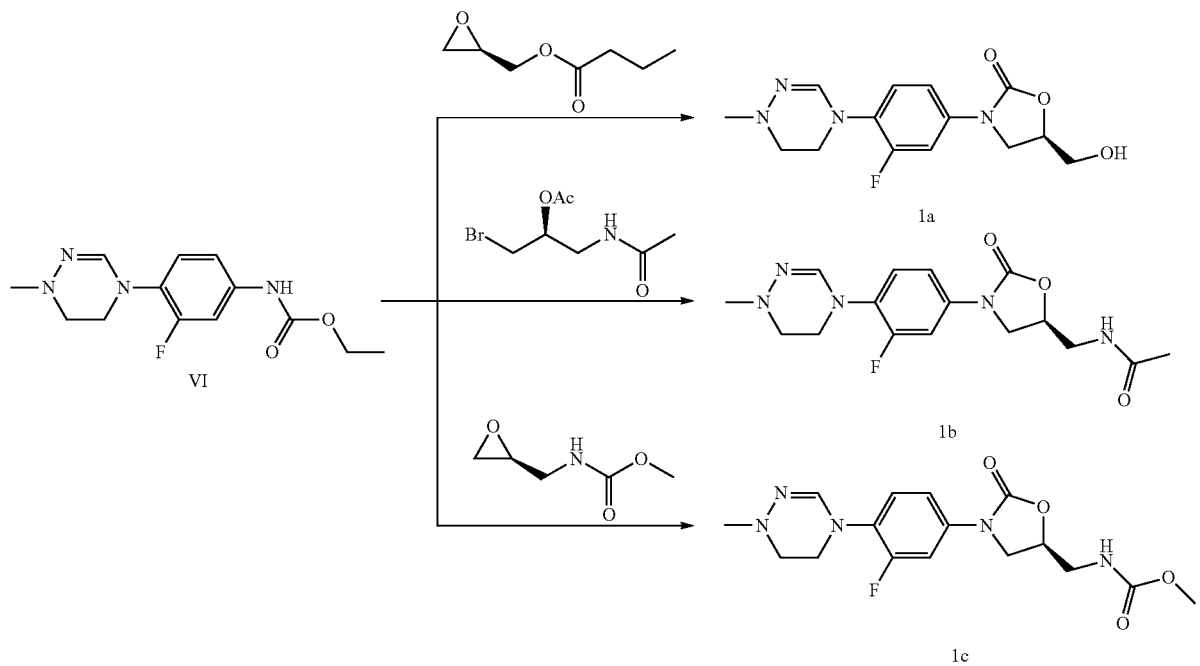

As shown in Reaction Formula 3, an appropriate method may be selected according to a kind of substituent R of Chemical Formula 1. For example, in the case of compound 1a in which R is hydroxyl group, a method of using (R)-glycidyl butyrate is appropriate, and in the case of compound 1b in which R is N-acetyl, a method of using (S)—N-(3-bromo-2-acetoxypropyl)acetamide is appropriate. Particularly, a synthetic method of the compound 1b has been well known and commonly used in recently applied Patent EP 2072513 A1, EP 2072514 A1, EP2141161 A1, EP 2141162 A1, and a detailed experimental method was disclosed therein. Further, in the case of compound 1c in which R is carbamate, an oxiranylcarbamate compound may be used.

In addition, all of these compounds may be synthesized from the compound 1a as shown in the following Reaction Formula 4.

[Reaction Formula 4]

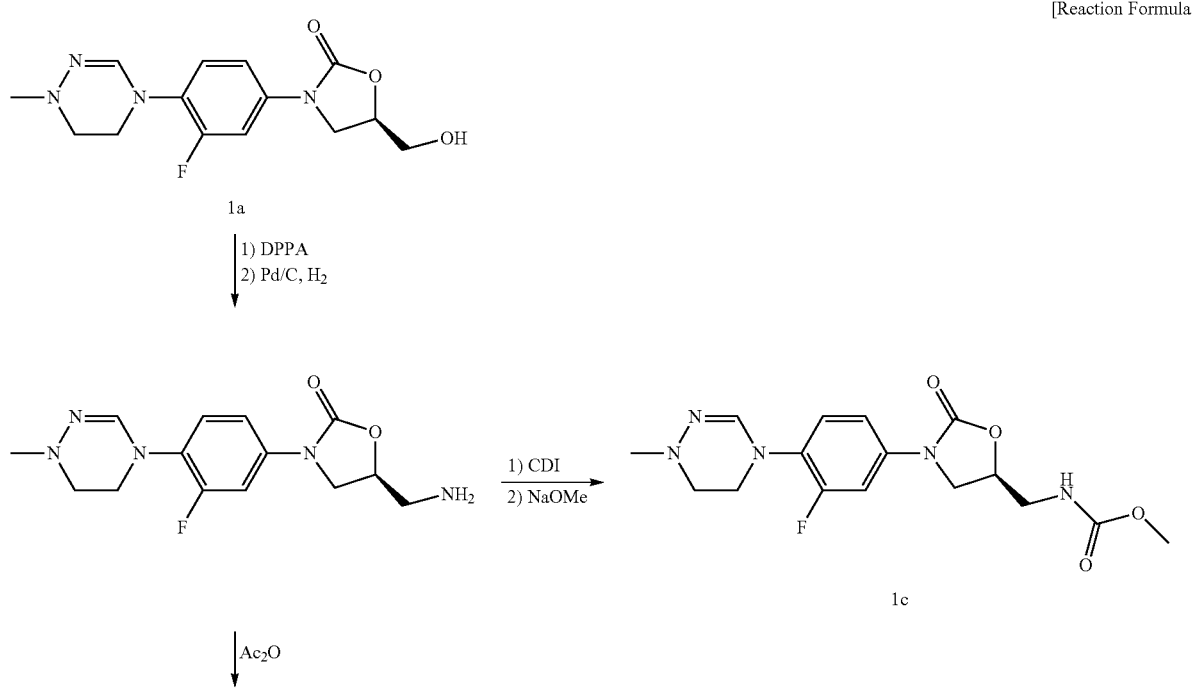

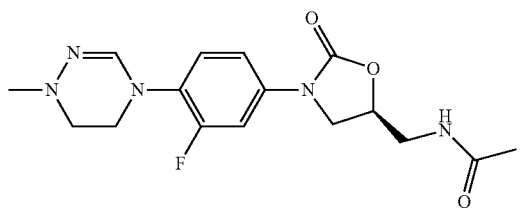

1b

As shown in the Reaction Formula 4, the compounds of Chemical Formula 1 may form various derivatives such as the compound 1b or the compound 1c from the compound 1a. Particularly, the carbamate compound such as the compound 1c is preferably synthesized using this method.

As a base used in synthesizing the compound 1a, butyllithium or lithium t-butoxide, and preferably, lithium t-butoxide may be used. As a solvent used in the reaction, THF or dimethylformamide (DMF) may be used, and preferably, a mixture of THF and DMF may be used. More preferably, THF and DMF may be used in a ratio of 2:1.

A synthesis of the compounds 1b and 1c is performed as follows. 1.3 equivalents of each of triphenylphosphine, diisopropyl azodicarboxylate (DIAD), and diphenylphophorylazide (DPPA) were put into THF solvent to prepare an azido compound, and then an amine compound was obtained by hydrogenating the azido compound using a Pd/C catalyst. When the amine compound obtained as described above was reacted with $Ac_2O$, the compound 1b was prepared, and when the amine compound was reacted with 2 to 3 equivalents of carbonyl diimidazole and then 1 equivalent of methoxide was added thereto in methanol solvent, the compound 1c was prepared.

The derivatives of Chemical Formula 1 may be prepared as various salt forms. Here, possible salts include all of the salts that may be used as a drug. A pharmaceutically acceptable salt includes an acid addition salt formed by a pharmaceutically acceptable free acid. As the free acid, both of an inorganic acid and an organic acid may be used. For example, the used inorganic acid is hydrochloric acid, bromic acid, sulfuric acid, phosphoric acid, or the like, and the used organic acid is citric acid, acetic acid, lactic acid, maleic acid, umaric acid, gluconic acid, methanesulfonic acid, glycolic acid, succinic acid, 4-toluenesulfonic acid, trifluoroacetic acid, galacturonic acid, embonic acid, glutamic acid, aspartic acid, or the like. Further, the present invention includes hydrates of the salt of oxazolidinone derivatives, and particularly, in the case in which the salt has hygroscopicity, hydrate form thereof having crystallization may be usefully used.

The solvent and the agent used in the present invention may be substituted with a functional substitute or derivative thereof that is known in the art, and reaction conditions such as a reaction time, a reaction temperature, and the like may be adjusted in order to optimize the reaction. Similarly to the present invention, a product may be separated from the reaction. In some cases, the product may be additionally purified by a general method in the art such as extraction, crystallization, trituration, or the like.

Advantageous Effects

As set forth above, the present invention relates to a method for preparing oxazolidinone derivatives acting as antibiotics against resistant bacteria such as methicillin-resistant staphylococci (MRSA) and vancomycin resistant enterococci (VRE). In addition, since the compounds of the present invention may include a cyclic amidrazone group to thereby be prepared as a salt form, the compounds have higher aqueous solubility as compared to the existing compound in the art, such that it is easy to develop the compound as oral drug or injection.

In the method for preparing of oxazolidinone derivatives having a cyclic amidrazone group or pharmaceutically acceptable salts thereof according to the present invention, the total yield may be increased, and (R)-3-(3-fluoro-4-(1-methyl-5,6-dihydro-1,2,4-triazin-4(1H)-yl)phenyl)-5-(substituted methyl)oxazolidin-2-one derivatives may be economically prepared in high purity as compared to the related art using a crystallization method or an extraction method appropriate for an industrial scale synthesis in a separating and purifying method.

BEST MODE

Hereinafter, in order to assist in understanding the present invention, preferable examples and experimental examples are described. However, the following examples and experimental examples are provided only for easily understanding the present invention. Therefore, the present invention is not limited thereto.

EXAMPLE 1

Preparation of the compound 1a of Chemical Formula 1 {(R)-3-(3-fluoro-4-(1-methyl-5,6-dihydro-1,2,4-triazine-4(1H)-yl)phenyl)-5-(hydroxymethyl)oxazolidine-2-one}

Synthesis of Compound I 3,4-difluoronitrobenzene (158 g, 0.99 mol, Aldrich.com) was dissolved in acetonitrile (800 mL), and then ethanolamine (117 g, 1.9 mol) was added thereto, followed by refluxing and stirring for 4 hours. The reactant was cooled to room temperature and then concentrated under reduced pressure. Then the resultant was triturated with diethylether and filtered, thereby obtaining a yellow compound I (199 g, 0.99 mol, 100%).

$^1$H NMR (400 MHz, chloroform-$d_1$) δ=7.97 (d, J=8.8 Hz, 1H), 7.87 (dd, $J_1$=11.6 Hz, $J_2$=2.4 Hz, 1H), 6.65 (t, J=8.8 Hz, 1H), 5.10-4.87 (br s, 1H), 3.97-3.83 (m, 2H), 3.43-3.37 (m, 2H)

LCMS: 201 (M+H$^+$) for $C_8H_9$—$FN_2O_3$

Synthesis of Compound II-1 (X=OMs)

The compound I ((37.7 g, 188 mmol) was dissolved in dichloromethane (400 ml), and then TEA (39.7 mL, 283 mmol) was added thereto at 0° C., followed by slow addition of Ms-Cl (17.5 mL, 226 mmol). After stirring for 30 minutes, the resultant was diluted with dichloromethane (400 mL) and washed with distilled water (500 mL), and the water layer was again extracted with dichloromethane (400 ml×3). The organic layer was dried over $Na_2SO_4$ and filtered, followed by concentration under reduced pressure, thereby obtaining Compound II-1 (52.5 g, 99%) as yellow solid.

$^1$H NMR (600 MHz, chloroform-$d_1$) δ=7.99 (d, J=9.0 Hz, 1H), 7.90 (dd, $J_1$=11.4 Hz, $J_2$=2.4 Hz, 1H), 6.67 (t, J=9.0 Hz, 1H), 4.99 (br s, 1H), 4.43 (t, J=5.4 Hz, 2H), 3.65 (q, J=5.4 Hz, 2H), 3.04 (s, 3H)

LCMS: 279 (M+H$^+$) for $C_9H_{11}$—$FN_2O_5S$

Synthesis of Compound III

While putting the compound II-1 (52.5 g, 188 mmol) into EtOH (300 mL) and stirring, DIPEA (32.8 mL, 188 mmol) was added thereto, and then 40% aqueous methyl hydrazine solution (75 mL, 570 mmol) was added thereto, followed by refluxing and stirring for 2 hours. The solvent was concentrated under reduced pressure, and then diluted with dichloromethane (400 mL). Then, the resultant was washed with sat. $NaHCO_3$ (400 mL). After the water layer was again extracted with dichloromethane (250 mL), the organic layer was collected to be dried over $Na_2SO_4$ and then filtered, followed by concentration under reduced pressure, thereby obtaining Compound III (42.9 g, 100%) as yellow solid.

$^1$H NMR (600 MHz, chloroform-$d_1$) δ=7.99 (dd, $J_1$=9.0 Hz, $J_2$=2.4 Hz, 1H), 7.86 (dd, $J_1$=11.4 Hz, $J_2$=2.4 Hz, 1H), 6.61 (t, J=9.0 Hz, 1H), 5.93 (br s, 1H), 3.89 (q, J=5.4 Hz, 2H), 2.99 (br s, 2H), 2.72 (t, J=5.4 Hz, 2H), 2.58 (s, 3H)

LCMS: 229 (M+H$^+$) for $C_9H_{13}$—$FN_4O_2$

Synthesis of Compound IV

The compound III (42.9 g, 188 mmol) was put into AcOH (200 mL) and trimethyl orthoformate (206 mL, 1.88 mol), followed by refluxing and stirring for 15 hours. The solvent was concentrated under reduced pressure and diluted with ethyl acetate (700 mL). Then, distilled water (500 mL) was added thereto and $Na_2CO_3$ was added thereto so that pH of the solution is 8 to 9, followed by separation of the organic layer using a separating funnel. The water layer was again extracted with ethyl acetate (300 mL), and the organic layer was collected to be dried over $Na_2SO_4$, followed by filtration using a tube filled with silica at a thickness of about 5 cm and concentration under reduced pressure, thereby obtaining Compound IV (34.5 g, 77%) as red solid.

$^1$H NMR (400 MHz, chloroform-$d_1$) δ=8.07-7.99 (m, 2H), 7.13 (m, 2H), 3.93 (m, 2H), 3.08 (m, 2H), 2.83 (s, 3H)

LCMS: 239 (M+H$^+$) for $C_{10}H_{11}$—$FN_4O_2$

Synthesis of Compound V

The compound IV (34.5 g, 145 mmol) was put into MeOH (400 mL), and 10% Pd/C (10 g) was added thereto. Then, a flask was equipped with a hydrogen balloon, and the reactant was stirred for 4 hours at room temperature. Pd/C was removed through filtering under reduced pressure using celite, and the filtrate was concentrated under reduced pressure, thereby obtaining Compound V (29.3 g, 97%) as orange solid.

$^1$H NMR (600 MHz, chloroform-$d_1$) δ=6.92 (t, J=9.0 Hz, 1H), 6.77 (s, 1H), 6.44-6.39 (m, 2H), 3.78 (br s, 2H), 3.73 (t, J=4.8 Hz, 2H), 2.94 (t, J=4.8 Hz, 2H), 2.77 (s, 3H)

LCMS: 209 (M+H$^+$) for $C_{10}H_{13}$—$FN_4$

Synthesis of Compound VI (R'=—$CH_2CH_3$)

While carbonyl diimidazole (46 g, 282 mmol) was put into dichloromethane (400 mL) and stirred, the compound V (29.3 g, 141 mmol) was slowly added thereto. This solution was stirred for 3 hours at room temperature and concentrated under reduced pressure until 200 ml of the solution was left. Next, EtOH (200 mL) was added thereto, followed by concentration under reduced pressure once more. EtOH (400 mL) was added again to this solution to be heated for 4 hours at 50° C. The temperature was cooled to room temperature, followed by concentration under reduced pressure, and then the resultant was diluted with ethyl acetate (400 mL), and 6N HCl was added thereto until pH of the resultant was 6. After the organic layer was separated, the water layer was extracted again with dichloromethane (300 mL×6). The organic layer was collected to be dried over $Na_2SO_4$, and the resultant was filtered, followed by concentration under reduced pressure, thereby obtaining Compound VI (30.5 g, 77%) as white solid.

$^1$H NMR (600 MHz, chloroform-$d_1$) δ=7.40 (br d, J=12.6 Hz, 1H), 7.03 (t, J=9.0 Hz, 1H), 7.00 (br dd, $J_1$=9.0 Hz, $J_2$=1.8 Hz, 1H), 6.88 (s, 1H), 6.76 (s, 1H), 4.23 (q, J=7.2 Hz, 2H), 3.80 (t, J=4.8 Hz, 2H), 2.97 (t, J=4.8 Hz, 2H), 2.78 (s, 3H), 1.31 (t, J=7.2 Hz, 3H)

LCMS: 281 (M+H$^+$) for $C_{13}H_{17}$—$FN_4O_2$

Synthesis of Compound 1a

While the compound VI (30.5 g, 109 mmol) was put into a mixing solution of THF (300 mL) and DMF (150 mL) and was stirred, MeOH (8.8 mL, 218 mmol) and tBuOLi (26.1 g, 327 mmol) were slowly added thereto over 10 minutes at 0° C., followed by stirring for 20 minutes. (R)-glycidyl butyrate (31.4 mL, 218 mmol) was added to this solution and stirred for 10 hours at room temperature. Sat. $NH_4Cl$ (100 mL) was added to this solution and neutralized with 1N HCL, and the reactant was concentrated under reduced pressure. After the resultant was diluted with ethyl acetate (400 mL) and then was washed with distilled water (300 mL). The water layer was extracted again with dichloromethane (300 mL×4). After the organic layer was collected to be dried over $Na_2SO_4$, the resultant was filtered, followed by concentration under reduced pressure. Then, the filtrate was triturated with hexane and washed with ethylether. After this solid was heated again in isopropanol, a solid formed by cooling the resultant was filtered, thereby obtaining Compound 1a (22.5 g, 67%) as white solid.

$^1$H NMR (600 MHz, DMSO-$d_6$) δ=7.59 (dd, $J_1$=13.8 Hz, $J_2$=2.4 Hz, 1H), 7.33-7.30 (m, 2H), 6.84 (s, 1H), 5.23 (t, J=5.4 Hz, 1H), 4.70 (m, 1H), 4.07 (t, J=9.0 Hz, 1H), 3.82 (m, 1H), 3.71 (t, J=4.8 Hz, 2H), 3.69-3.54 (m, 2H), 2.87 (t, J=4.8 Hz, 2H), 2.61 (s, 3H)

LCMS: 309 (M+H$^+$) for $C_{14}H_{17}$—$FN_4O_3$

EXAMPLE 2

Preparing Method Using the Compound of Chemical Formula II-2 as the Intermediate

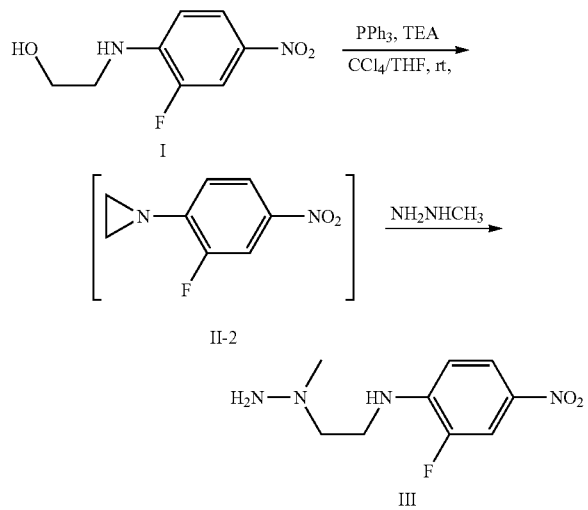

After the compound I (24.2 kg, 121 mol) was dissolved in THF (130 kg), triphenylphosphine (41 kg, 156 mol) and TEA (24.5 kg, 242 mol) were added thereto at 10 to 15° C. Then, CCl$_4$ (37.3 kg) was again added thereto, and the temperature was slowly raised to room temperature over 1 hour, followed by stirring for one day. After the reaction was terminated, next step was immediately progressed.

Methyl hydrazine (44.5 kg, 966 mmol) was put into the reaction solution at 10 to 15° C. and stirred for 5 hours. Then, the mixture was stirred for 24 hours at room temperature and stirred for 10 hours at 35 to 40° C. After the reaction was terminated, the temperature was cooled to room temperature, followed by adding distilled water (100 Kg) thereto while stirring. Then, the resultant was left so that layers were separated from each other. The THF layer was separated to thereby be washed with distilled water (50 kg), followed by drying over Na$_2$SO$_4$ (20 kg) for 5 hours. Then, the resultant was filtered, thereby obtaining Compound III (11.5 kg, 50 mol, yield: 41%) in two steps.

EXAMPLE 3

Preparation of Compound 1c of Chemical Formula 1

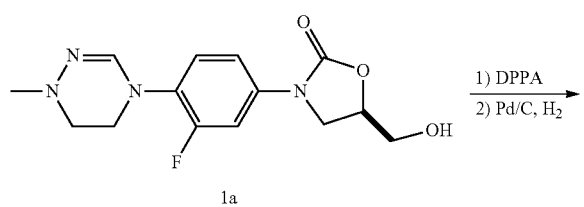

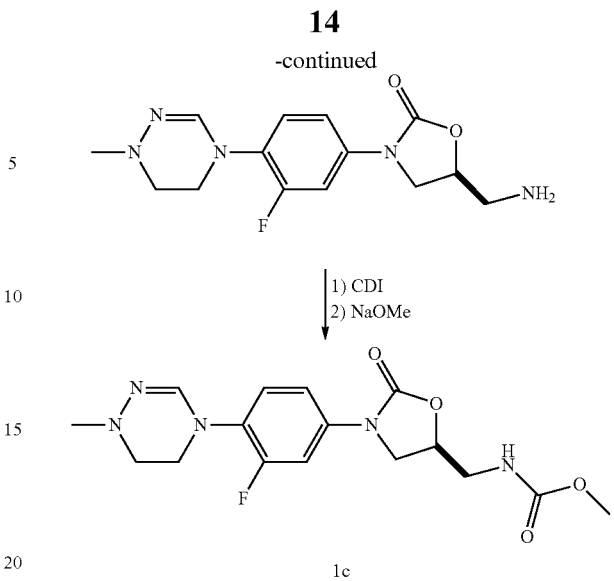

While the compound 1a (7 g, 22.7 mmol) and triphenylphosphine (7.7 g, 29.5 mmol) were put into tetrahydrofuran (100 mL) and stirred, DIAD (5.8 mL, 29.5 mmol) and diphenylphosphorylazide (DPPA, 5.1 mL, 29.5 mmol) were sequentially slowly added thereto at 0° C. and stirred for 1.5 hours at room temperature. Distilled water (50 mL) was added to this solution and stirred for 5 minutes, and the mixture was concentrated under reduced pressure until a half of the solution was left. Then, the resultant was diluted with ethylacetate and washed with sat. NaHCO$_3$. The organic layer was dried over Na$_2$SO$_4$ and filtered, followed by concentration under reduced pressure, and then silica-filtered, thereby obtaining an azido compound (6.1 g, 81%) as white solid.

The azido compound (6.1 g, 18.3 mmol) obtained as described above was put into methanol (250 mL) together with Pd/C (0.9 g) and stirred for 1.5 hours under hydrogen balloon. This solution was celite-filtered and concentrated to quantitatively obtain an amine compound.

The amine compound obtained as described above was dissolved in dichloromethane (100 mL) and then dropped into a solution in which CDI (8.9 g, 54.9 mmol) was dissolved in dichloromethane (150 mL), followed by stirring for 30 minutes at room temperature. Methanol (150 mL) was added to this solution and concentrated under reduced pressure, and again 400 mL of methanol was added thereto. The resultant was concentrated under reduced pressure until about 200 mL of methanol was left, followed by removal of dichloromethane. Then, 1M NaOMe (18.3 mL) was added thereto and stirred for 1 hour at room temperature. After this solution was concentrated under reduced pressure and then dissolved in ethyl acetate (100 mL), distilled water (100 mL) was added thereto and neutralized with 4N HCL. The water layer was extracted again with dichloromethane (300 mL×3). The organic layer was collected to be dried over Na$_2$SO$_4$ and then filtered, followed by concentration under reduced pressure, and then silica-filtered, thereby obtaining Compound 1c (3 g, 45%) as white solid.

$^1$H NMR (400 MHz, CDCl$_3$) δ=7.49 (dd, J$_1$=9.0 Hz, J$_2$=1.4 Hz, 1H), 7.14 (dd, J$_1$=6.0 Hz, J$_2$=1.4 Hz, 1H), 7.08 (t, J=6.0 Hz, 1H), 6.87 (s, 1H), 5.08 (br t, 1H), 4.76 (m, 1H), 4.01 (t, J=6.0 Hz, 1H), 3.80-3.76 (m, 3H), 3.66 (s, 3H), 3.64-3.51 (m, 2H), 2.96 (t, J=3.2 Hz, 2H), 2.76 (s, 3H)

LCMS: 366 (M+H$^+$) for C$_{16}$H$_{20}$FN$_5$O$_4$

[Industrial Applicability]

The present invention relates to a method for preparing oxazolidinone derivatives acting as antibiotics against resistant bacteria such as methicillin-resistant staphylococci (MRSA) and vancomycin resistant enterococci (VRE). In addition, since the compounds of the present invention may include a cyclic amidrazone group to thereby be prepared as a salt form, the compounds have higher aqueous solubility as compared to the existing compound in the art, such that it is easy to develop the compound as oral drug or injection.

In the method for preparing of oxazolidinone derivatives having a cyclic amidrazone group or pharmaceutically acceptable salts thereof according to the present invention, the total yield may be increased, and (R)-3-(3-fluoro-4-(1-methyl-5,6-dihydro-1,2,4-triazin-4(1H)-yl)phenyl)-5-(substituted methyl)oxazolidin-2-one derivatives may be economically prepared in high purity as compared to the related art using a crystallization method or an extraction method appropriate for an industrial scale synthesis in a separating and purifying method.

The invention claimed is:
1. A method for preparing an oxazolidinone compound having a cyclic amidrazone group of Chemical Formula 1, and pharmaceutically acceptable salts thereof, the method comprising:
  1) reacting 3,4-difluoronitrobenzene with ethanolamine to prepare a compound of Chemical Formula I;
  2) reacting the compound of Chemical Formula I with an agent containing a leaving group X to convert an alcohol group of the compound of Chemical Formula I into the leaving group X, thereby preparing a compound of Chemical Formula II-1, or subjecting the compound of Chemical Formula I to a reduction reaction in the presence of base to prepare an aziridine compound of Chemical Formula II-2;
  3) reacting the compound of Chemical Formula II-1 or the compound of Chemical Formula II-2 with methyl hydrazine to prepare a compound of Chemical Formula III;
  4) reacting the compound of Chemical Formula III with trimethyl orthoformate to prepare a cyclic amidrazone of Chemical Formula IV;
  5) reducing a nitro group of the cyclic amidrazone compound of Chemical Formula IV to prepare an amine compound of Chemical Formula V;
  6) sequentially reacting the amine compound of Chemical Formula V with carbonyl diimidazole and R'—OH [R'= (C1-C6)alkyl or (C6-C12)arylC1-C6)alkyl] to convert an amine group of the compound of Chemical Formula V into carbamate, thereby preparing the compound of a compound of Chemical Formula VI; and
  7) cyclizing the compound of Chemical Formula VI to prepare an oxazolidinone compound of Chemical Formula 1

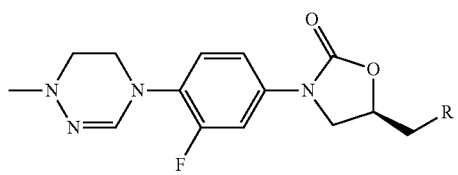

Chemical Formula 1

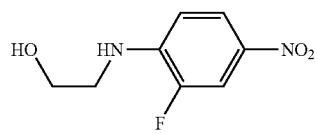

Chemical Formula I

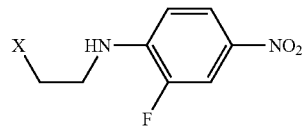

Chemical Formula II-1

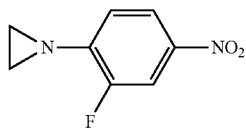

Chemical Formula II-2

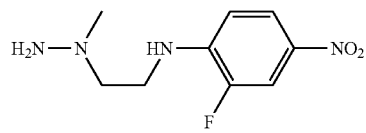

Chemical Formula III

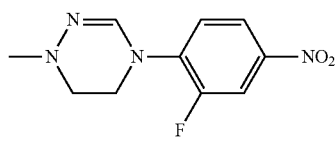

Chemical Formula IV

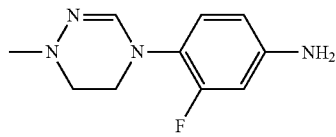

Chemical Formula V

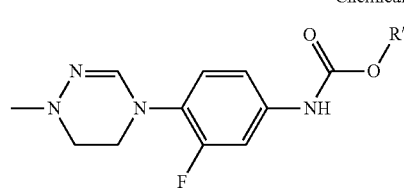

Chemical Formula VI wherein

X is a halogen, substituted or un-substituted (C1-C6) alkanesulfonyloxy, or substituted or un-substituted (C6-C 12)arylsulfonyloxy;

R is OH or NHC(=O)R$_1$;

R$_1$ is a (C1-C6)alkyl or (C1-C6)alkoxy; and

R' is a (C1-C6)alkyl or (C6-C12)aryl(C1-C6)alkyl.

2. The method of claim 1, further comprising reacting an amine compound obtained by reacting the following compound of Chemical Formula 1a in the presence of triphenylphosphine, diisopropyl azodicarboxylate, and diphenylphophorylazide, and then hydrogenating the reactant with an acetic anhydride, thereby preparing a compound of Chemical Formula 1b Chemical Formula 1a

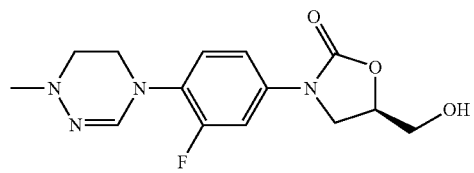

Chemical Formula 1b

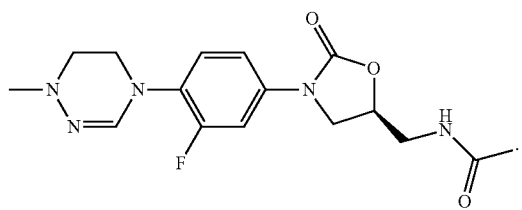

3. The method of claim 1, further comprising sequentially reacting an amine compound obtained by reacting the following compound of Chemical Formula 1a in the presence of triphenylphosphine, diisopropyl azodicarboxylate, and diphenylphophorylazide and then hydrogenating the reactant with carbonyl diimidazole and (C1-C6)alkoxide, thereby preparing a compound of Chemical Formula 1c Chemical Formula 1a

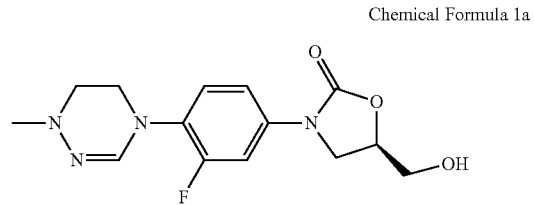

Chemical Formula 1c

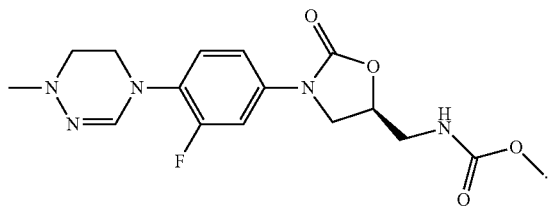

4. A cyclic amidrazone compound represented by the following Chemical Formula IV:

Chemical Formula IV

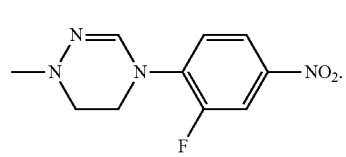

5. A cyclic amidrazone compound represented by the following Chemical Formula VI:

Chemical Formula VI

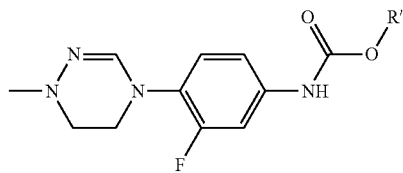

wherein R' is a (C1-C6)alkyl or (C6-C12)aryl(C1-C6)alkyl.

* * * * *